United States Patent
Sela et al.

(10) Patent No.: US 10,074,176 B2
(45) Date of Patent: *Sep. 11, 2018

(54) METHOD, SYSTEM AND APPARATUS FOR DISPLAYING SURGICAL ENGAGEMENT PATHS

(71) Applicant: SYNAPTIVE MEDICAL (BARBADOS) INC., Bridgetown (BB)

(72) Inventors: Gal Sela, Toronto (CA); Neil Witcomb, Toronto (CA); David Gallop, Toronto (CA); Kelly Noel Dyer, Toronto (CA); Wes Hodges, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

This patent is subject to a terminal disclaimer.

(21) Appl. No.: 15/358,796

(22) Filed: Nov. 22, 2016

(65) Prior Publication Data

US 2017/0076450 A1 Mar. 16, 2017

Related U.S. Application Data

(63) Continuation of application No. 14/555,636, filed on Nov. 27, 2014, now Pat. No. 9,536,309.

(51) Int. Cl.
*G06K 9/00* (2006.01)
*G06T 7/00* (2017.01)
(Continued)

(52) U.S. Cl.
CPC ............ *G06T 7/0012* (2013.01); *A61B 34/10* (2016.02); *G06F 19/321* (2013.01);
(Continued)

(58) Field of Classification Search
None
See application file for complete search history.

(56) References Cited

U.S. PATENT DOCUMENTS 6,390,097 B1 5/2002 Chandra
7,081,088 B2 * 7/2006 Geiger ................ G06F 19/3437
345/427
(Continued)

FOREIGN PATENT DOCUMENTS

CA 2899359 A1 9/2014
WO WO-2008030264 A1 3/2008

OTHER PUBLICATIONS

International Search Report dated Jan. 8, 2016 for International Paternt Application No. PCT/IB2015/058680.
(Continued)

*Primary Examiner* — Nancy Bitar
(74) *Attorney, Agent, or Firm* — Perry + Currier

(57) ABSTRACT

A method and computing device for displaying surgical path data are provided. The computing device includes an input device, a display, a memory and a processor. The memory stores (i) an image of a volume of patient tissue having an outer surface, and (ii) anatomical data defining anatomical features of the volume. The processor receives an identifier of a target location within the volume; generates a plurality of paths from the outer surface to the target location, each path having a start point located on the outer surface, and an end point at the target location; for each of the plurality of paths, determines a score based on a comparison between the path and the anatomical data; and controls the display to present the outer surface and, at the locations of the start points, indications of the respective scores of the paths corresponding to the start points.

15 Claims, 11 Drawing Sheets

(51) Int. Cl.
*A61B 34/10* (2016.01)
*G06F 19/00* (2018.01)
*G06T 7/20* (2017.01)
*G06T 19/00* (2011.01)
*G06K 9/46* (2006.01)
*G06K 9/52* (2006.01)
*G06K 9/62* (2006.01)

(52) U.S. Cl.
CPC ......... *G06K 9/4652* (2013.01); *G06K 9/4661* (2013.01); *G06K 9/52* (2013.01); *G06K 9/6267* (2013.01); *G06T 7/20* (2013.01); *G06T 19/003* (2013.01); *A61B 2034/107* (2016.02); *G06T 2207/10012* (2013.01); *G06T 2207/10028* (2013.01); *G06T 2207/10048* (2013.01); *G06T 2207/30016* (2013.01); *G06T 2207/30096* (2013.01); *G06T 2207/30101* (2013.01); *G06T 2207/30204* (2013.01); *G06T 2210/41* (2013.01)

(56) References Cited

U.S. PATENT DOCUMENTS

| | | | | |
|---|---|---|---|---|
| 7,558,622 | B2* | 7/2009 | Tran | A61B 5/0022 |
| | | | | 600/509 |
| 8,077,144 | B2* | 12/2011 | Honda | G06F 3/048 |
| | | | | 345/156 |
| 8,942,454 | B2* | 1/2015 | Wen | G06T 5/50 |
| | | | | 382/131 |
| 9,536,309 | B2* | 1/2017 | Sela | G06T 7/0012 |
| 9,734,632 | B2* | 8/2017 | Thomas | G06T 19/003 |
| 2008/0183073 | A1 | 7/2008 | Higgins et al. | |
| 2009/0253984 | A1* | 10/2009 | Yui | A61B 5/055 |
| | | | | 600/420 |
| 2009/0259230 | A1 | 10/2009 | Khadem et al. | |
| 2011/0245825 | A1 | 10/2011 | Mitzlaff et al. | |
| 2013/0085344 | A1 | 4/2013 | Merkl et al. | |

OTHER PUBLICATIONS

Written Opinion dated Jan. 8, 2016 for International Patent Application No. PCT/IB2015/058680.

* cited by examiner

METHOD, SYSTEM AND APPARATUS FOR DISPLAYING SURGICAL ENGAGEMENT PATHS

CROSS REFERENCE TO RELATED APPLICATIONS

This application claims priority from U.S. application Ser. No. 14/555,636, filed Nov. 27, 2014, the contents of which are incorporated by reference.

FIELD

The specification relates generally to surgical planning, and specifically to a method, system and apparatus for displaying surgical paths.

BACKGROUND

Minimally invasive surgical techniques can substantially reduce the risk of injury to patients, in comparison with traditional surgical techniques. The possibility for patient injury remains, however, particularly during the insertion of ports or other instruments through patient tissue to initiate the minimally invasive procedures. The likelihood of patient injury can be reduced by careful selection of an insertion site for the instruments, and definition of a trajectory to a targeted area. However, current surgical planning and navigation systems may not provide sufficient information to allow the selection of an optimal insertion site.

SUMMARY

According to an aspect of the specification, a method is provided of displaying surgical path data in a computing device having an input device, a display, a memory and a processor interconnected with the input device, the display, and the memory, the method comprising: storing, in the memory, (i) an image of a volume of patient tissue having an outer surface, and (ii) anatomical data defining anatomical features of the volume; receiving, at the processor, an identifier of a target location within the volume; at the processor, generating a plurality of paths from the outer surface to the target location, each path having a start point located on the outer surface, and an end point at the target location; for each of the plurality of paths, determining a score at the processor based on a comparison between the path and the anatomical data; and controlling the display to present the outer surface and, at the locations of the start points, indications of the respective scores of the paths corresponding to the start points.

According to a further aspect of the specification, a non-transitory computer-readable medium is provided storing a plurality of computer-readable instructions for execution by a processor of a computing device having an input device, a display, and a memory connected to the processor, to perform the above method.

According to another aspect of the specification, a computing device is provided for displaying surgical path data, comprising: an input device; a display; a memory storing (i) an image of a volume of patient tissue having an outer surface, and (ii) anatomical data defining anatomical features of the volume; and a processor interconnected with the input device, the display, and the memory, the processor configured to: receive an identifier of a target location within the volume; generate a plurality of paths from the outer surface to the target location, each path having a start point located on the outer surface, and an end point at the target location; for each of the plurality of paths, determine a score based on a comparison between the path and the anatomical data; and control the display to present the outer surface and, at the locations of the start points, indications of the respective scores of the paths corresponding to the start points.

BRIEF DESCRIPTIONS OF THE DRAWINGS

Embodiments are described with reference to the following figures, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein the term "intraoperative" refers to an action, process, method, event or step that occurs or is carried out during at least a portion of a medical procedure. The term "preoperative" as used herein refers to an action, process, method, event or step that occurs or is carried out before the medical procedure begins. The terms intraoperative and preoperative, as defined herein, are not limited to surgical procedures, and may refer to other types of medical procedures, such as diagnostic and therapeutic procedures.

Figure 1:
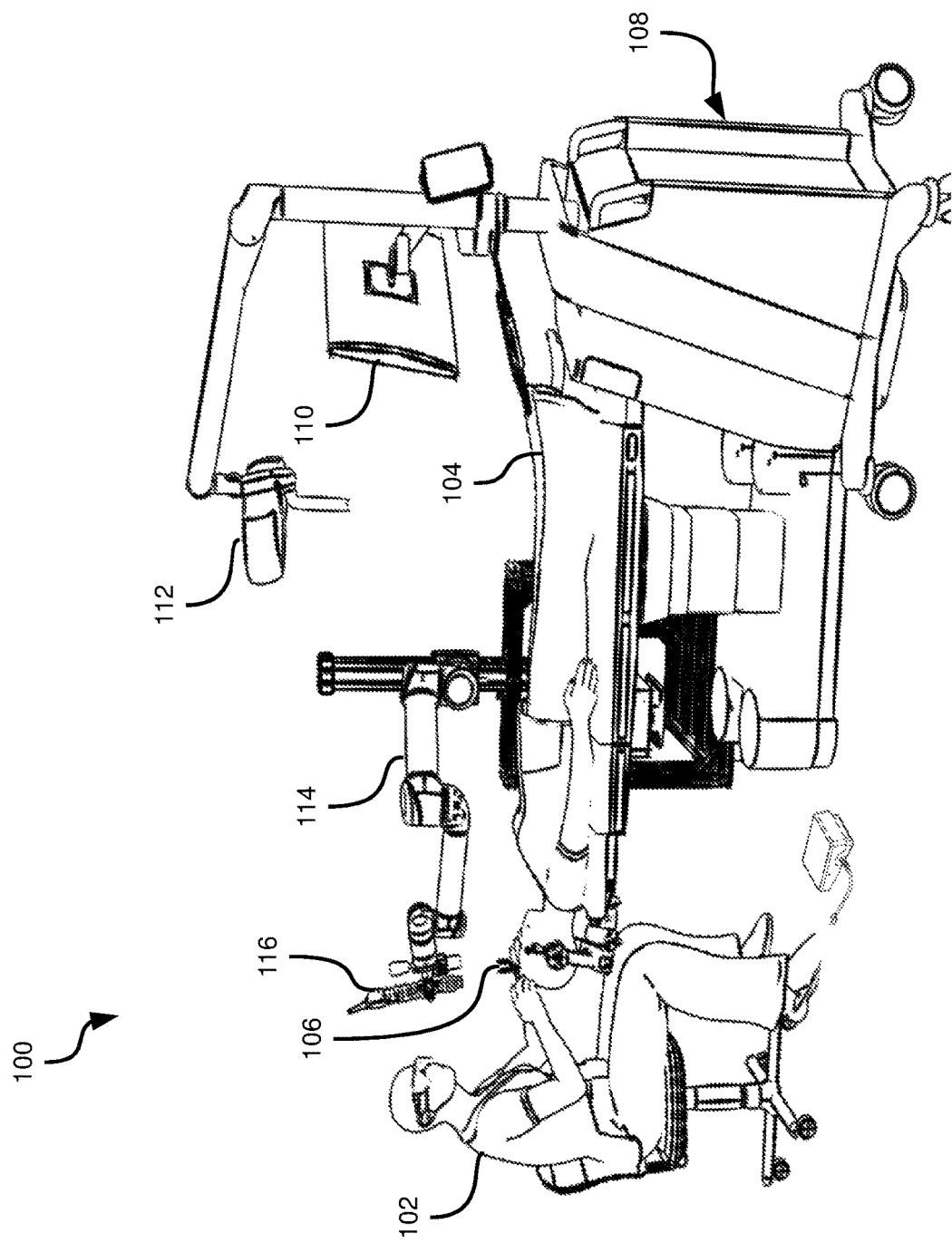
FIG. 1 depicts an operating theatre, according to a non-limiting embodiment.

FIG. 1 depicts a surgical operating theatre 100 in which a healthcare worker 102 (e.g. a surgeon) operates on a patient 104. Specifically, surgeon 102 is shown conducting a minimally invasive surgical procedure on the brain of patient 104. Minimally invasive brain surgery involves the insertion and manipulation of instruments into the brain through an opening that is significantly smaller than the portions of skull removed to expose the brain in traditional brain surgery techniques. The description below makes reference to the brain of patient 104 as an example of tissue to which the techniques herein may be applied. It will be understood, however, that those techniques may also be applied to a wide variety of other tissues. Thus, when the brain of patient 104 is mentioned below, it is simply an example of the various tissues in connection with which the systems and methods herein may be implemented.

The opening through which surgeon 102 inserts and manipulates instruments is provided by an access port 106. Access port 106 typically includes a hollow cylindrical device with open ends. During insertion of access port 106 into the brain (after a suitable opening has been drilled in the skull), an introducer (not shown) is generally inserted into access port 106. The introducer is typically a cylindrical device that slidably engages the internal surface of access port 106 and bears a conical atraumatic tip to allow for insertion of access port 106 into the sulcal folds of the brain. Following insertion of access port 106, the introducer may be removed, and access port 106 may then enable insertion and bimanual manipulation of surgical tools into the brain. Examples of such tools include suctioning devices, scissors, scalpels, cutting devices, imaging devices (e.g. ultrasound sensors) and the like.

Also shown in FIG. 1 is an equipment tower 108 supporting a computing device (not shown) such as a desktop computer, as well as one or more displays 110 connected to the computing device for displaying images provided by the computing device.

Equipment tower 108 also supports a tracking system 112. Tracking system 112 is generally configured to track the positions of one or more reflective markers (not shown) mounted on access port 106, any of the above-mentioned surgical tools, or any combination thereof. Such markers, also referred to as fiducial markers, may also be mounted on patient 104, for example at various points on patient 104's head. Tracking system 112 may therefore include a camera (e.g. a stereo camera) and a computing device (either the same device as mentioned above or a separate device) configured to locate the fiducial markers in the images captured by the camera, and determine the spatial positions of those markers within the operating theatre. The spatial positions may be provided by tracking system 112 to the computing device in equipment tower 108 for subsequent use.

The nature of the markers and the camera are not particularly limited. For example, the camera may be sensitive to infrared (IR) light, and tracking system 112 may include one or more IR emitters (e.g. IR light emitting diodes (LEDs)) to shine IR light on the markers. In other examples, marker recognition in tracking system 112 may be based on radio frequency (RF) radiation, visible light emitted from devices such as pulsed or un-pulsed LEDs, electromagnetic radiation other than IR or visible light, and the like. For RF and EM-based tracking, each object can be fitted with markers having signatures unique to that object, and tracking system 112 can include antennae rather than the above-mentioned camera. Combinations of the above may also be employed.

Each tracked object generally includes three or more markers fixed at predefined locations on the object. The predefined locations, as well as the geometry of each tracked object, are configured within tracking system 112, and thus tracking system 112 is configured to image the operating theatre, compare the positions of any visible markers to the pre-configured geometry and marker locations, and based on the comparison, determine which tracked objects are present in the field of view of the camera, as well as what positions those objects are currently in. An example of tracking system 112 is the "Polaris" system available from Northern Digital Inc.

Also shown in FIG. 1 is an automated articulated arm 114, also referred to as a robotic arm, carrying an external scope 116 (i.e. external to patient 104). External scope 116 may be positioned over access port 106 by robotic arm 114, and may capture images of the brain of patient 104 for presentation on display 110. The movement of robotic arm 114 to place external scope 116 correctly over access port 106 may be guided by tracking system 112 and the computing device in equipment tower 108. The images from external scope 116 presented on display 110 may be overlaid with other images, including images obtained prior to the surgical procedure. The images presented on display 110 may also display virtual models of surgical instruments present in the field of view of tracking system 112 (the positions and orientations of the models having been determined by tracking system 112 from the positions of the markers mentioned above).

Before a procedure such as that shown in FIG. 1 (which may be, for example, a tumor resection), preoperative images may be collected of patient 104, or at least of patient 104's brain or portions thereof. Such preoperative images may be collected using any of a variety of imaging modalities, such as Magnetic Resonance Imaging (MRI), Optical Coherence Tomography (OCT), ultrasound, Computed Tomography (CT), optical spectroscopy and the like. For each of the above-mentioned imaging modalities, various imaging techniques may be used. Polarization Sensitive OCT and OCT elastography are exemplary uses of the OCT modality. Diffusion MRI (also referred to as diffusion tensor imaging, DTI) is an example use of the MRI modality. Raman spectroscopy is an example use of optical spectroscopy. A variety of other examples of the above modalities will also occur to those skilled in the art.

Preoperative images may be used for planning purposes. During the procedure, additional images (referred to as intraoperative images) may be collected of patient 104's brain, using any suitable ones of the above-mentioned modalities (it will be apparent to those skilled in the art that some imaging modalities are less suitable or unsuitable for preoperative use, while other imaging modalities are less suitable or unsuitable for intraoperative use).

An example of a planning activity that may be performed using preoperative images is the selection of an entry location (also referred to as an engagement location) at which access port 106 will be introduced into the brain (or other patient tissue) during the planned surgical procedure. Surgical procedures generally target particular areas of patient 104's brain (or other tissues). The targeted areas define the location of access port 106 following its insertion: when access port 106 has been fully inserted into the brain, the tip of access port 106 is preferably adjacent to the targeted area, so that instruments inserted through access port 106 can access the targeted area. Therefore, during insertion, the tip of access port 106 must travel from the outer surface of the brain into the brain until the targeted area has been reached. As will now be apparent to those skilled in the art, access port 106 may reach the targeted area via insertion at a wide variety of locations on the outer surface of the brain. Some of those locations may be more suitable than others, however.

As will be described in further detail below, the computing device housed in equipment tower 108 can perform various actions to evaluate the suitability of potential entry locations for access port 106, and to display the potential entry locations along with indications of their suitability.

Figure 2:
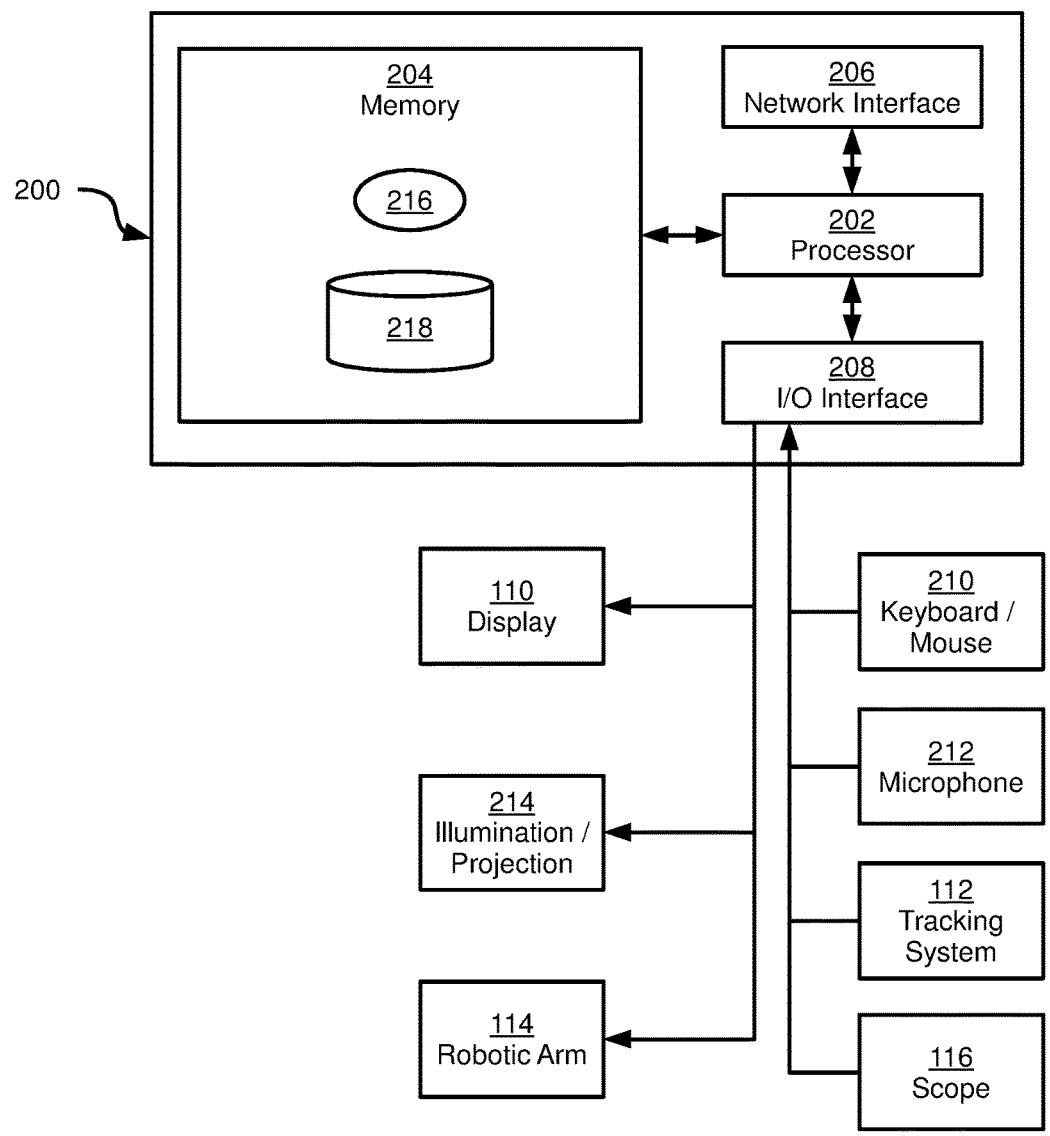
FIG. 2 depicts a computing device of the operating theatre of FIG. 1, according to a non-limiting embodiment.

Before a discussion of the functionality of the computing device, a brief description of the components of the computing device will be provided. Referring to FIG. 2, a computing device 200 is depicted, including a central processing unit (also referred to as a microprocessor or simply a processor) 202 interconnected with a non-transitory computer readable storage medium such as a memory 204.

Processor 202 and memory 204 are generally comprised of one or more integrated circuits (ICs), and can have a variety of structures, as will now occur to those skilled in the art (for example, more than one CPU can be provided). Memory 204 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 204 includes both a volatile memory and a non-volatile memory. Other types of non-transitory computer readable storage medium are also contemplated, such as compact discs (CD-ROM, CD-RW) and digital video discs (DVD).

Computing device 200 also includes a network interface 206 interconnected with processor 202. Network interface 206 allows computing device 200 to communicate with other computing devices via a network (e.g. a local area network (LAN), a wide area network (WAN) or any suitable combination thereof). Network interface 206 thus includes any necessary hardware for communicating over such networks, such as radios, network interface controllers (NICs) and the like.

Computing device 200 also includes an input/output interface 208, including the necessary hardware for interconnecting processor 202 with various input and output devices. Interface 208 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 208, computing device 200 is connected to input devices including a keyboard and mouse 210, a microphone 212, as well as scope 116 and tracking system 112, mentioned above. Also via interface 208, computing device 200 is connected to output devices including illumination or projection components 214 (e.g. lights, projectors and the like), as well as display 110 and robotic arm 114 mentioned above. Other input (e.g. touch screens) and output devices (e.g. speakers) will also occur to those skilled in the art.

It is contemplated that I/O interface 208 may be omitted entirely in some embodiments, or may be used to connect to only a subset of the devices mentioned above. The remaining devices may be connected to computing device 200 via network interface 206.

Computing device 200 stores, in memory 204, an engagement path evaluation application 216 (also referred to herein as application 216) comprising a plurality of computer readable instructions executable by processor 202. When processor 202 executes the instructions of application 216 (or, indeed, any other application stored in memory 204), processor 202 performs various functions implemented by those instructions, as will be discussed below. Processor 202, or computing device 200 more generally, is therefore said to be "configured" or "operating" to perform those functions via the execution of application 216.

Also stored in memory 204 are various data repositories, including a patient data repository 218. Patient data repository 218 can contain a surgical plan defining the various steps of the minimally invasive surgical procedure to be conducted on patient 104, as well as image data relating to patient 104, such as MRI and CT scans, three-dimensional models of the brain of patient 104, and the like. In the present embodiment, repository 218 includes at least an image of a volume of patient tissue having an outer surface, such as the brain of patient 104. Repository 218 also includes anatomical data defining anatomical features of the volume of tissue. The anatomical data can be included within the image, or can be stored separately from the image.

Figure 3:
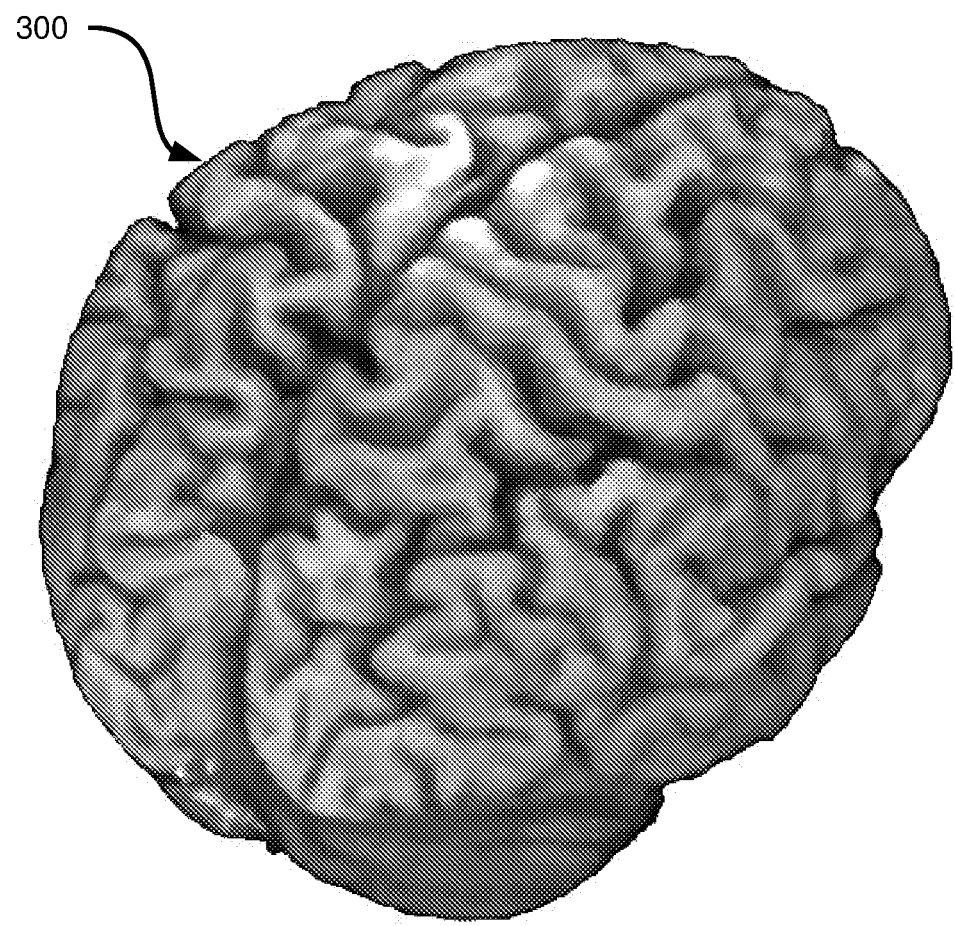
FIG. 3 depicts an image of a volume of tissue maintained by the computing device of FIG. 2, according to a non-limiting embodiment.

Referring to FIG. 3, an example image 300 of a volume of tissue stored in repository 218 is depicted. The volume of tissue is the brain of patient 104 in the present example, and image 300 is a three-dimensional image of the brain of patient 104 obtained via MRI scanning. As seen in FIG. 3, image 300 depicts an outer surface of the brain. Image 300 can also include image data depicting various internal structures of the brain, as well as structures surrounding the brain (such as the skull of patient 104).

Figure 4:
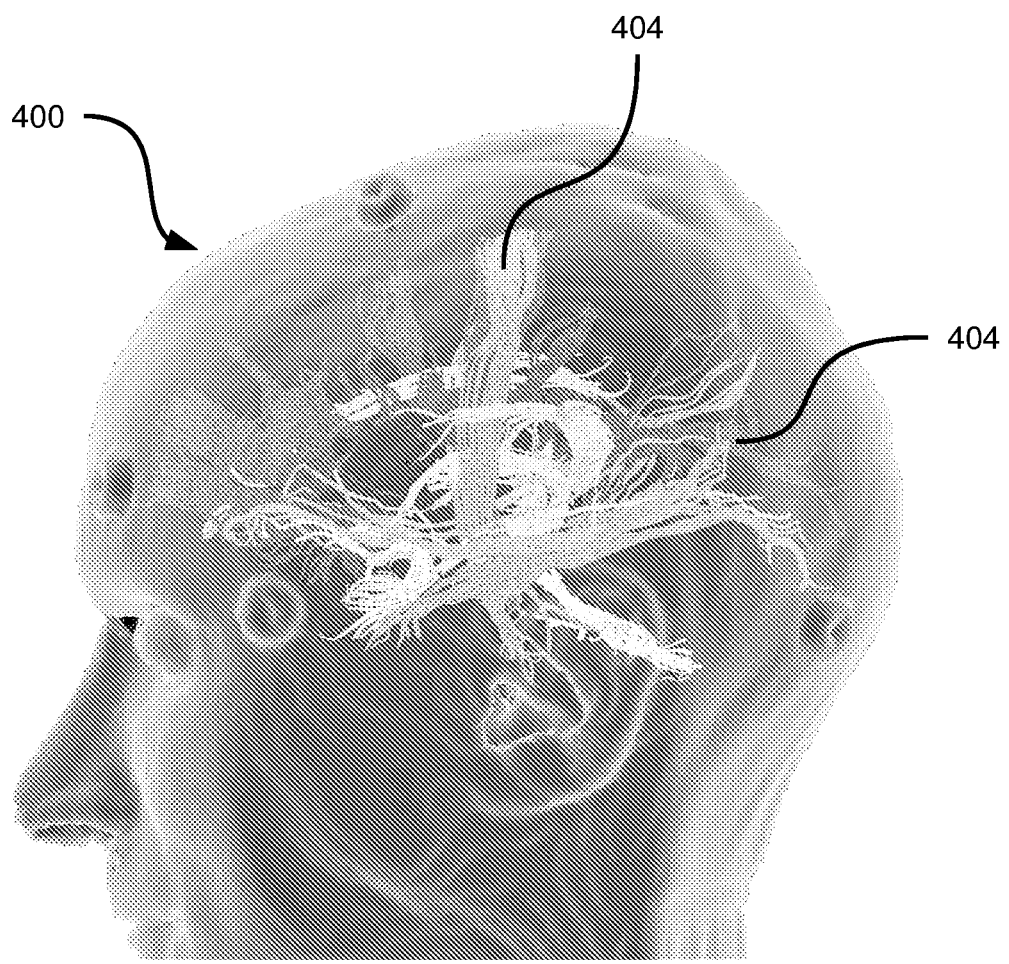
FIG. 4 depicts anatomical data maintained by the computing device of FIG. 2, according to a non-limiting embodiment.

Referring to FIG. 4, an example of anatomical data is shown. In particular, an image 400 of the head of patient 104 is shown (obtained via MRI scanning, for example). Image 400 defines anatomical features in the form of diffusion fibre tracts 404 within the brain of patient 104. Tracts 404 are areas of anisotropic diffusion (that is, directional diffusion) of fluid within the brain, and can be identified via a variety of imaging modalities. One such imaging modality is MRI, particularly using the diffusion tensor imaging technique during MRI scanning.

Tracts 404 are presented simply as an example of anatomical data; other anatomical data can also be stored in repository 218 defining other anatomical features. Examples of other anatomical features include the locations of sulcal folds in the patient 104's brain, the location of blood vessels in the patient 104's brain, and the locations of one or more regions of interest (ROIs) in the patient 104's brain. Such regions of interest can include any region within image 300, and can be defined in repository 218 by way of input data received via keyboard/mouse 210, or can be defined automatically by processor 202. For example, processor 202 can be configured to detect certain anatomical structures within image 300 and store their locations as ROIs in repository 218.

The anatomical data referred to above need not be stored in the form of images. For example, tracts 404 can be stored in a database of locations and diffusion intensities, instead of or in addition to in image 400. In addition, the anatomical data can be included within image 300 itself. For example, sulcal folds are visible in the outer surface of the brain depicted by image 300. Thus, image 300 itself contains anatomical data.

As mentioned above, computing device 200 is configured, via the execution of application 216 by processor 202, to perform various functions to define and evaluate various engagement paths for access port 106, and present those paths on display 110. Those functions will be described in further detail below.

Figure 5:
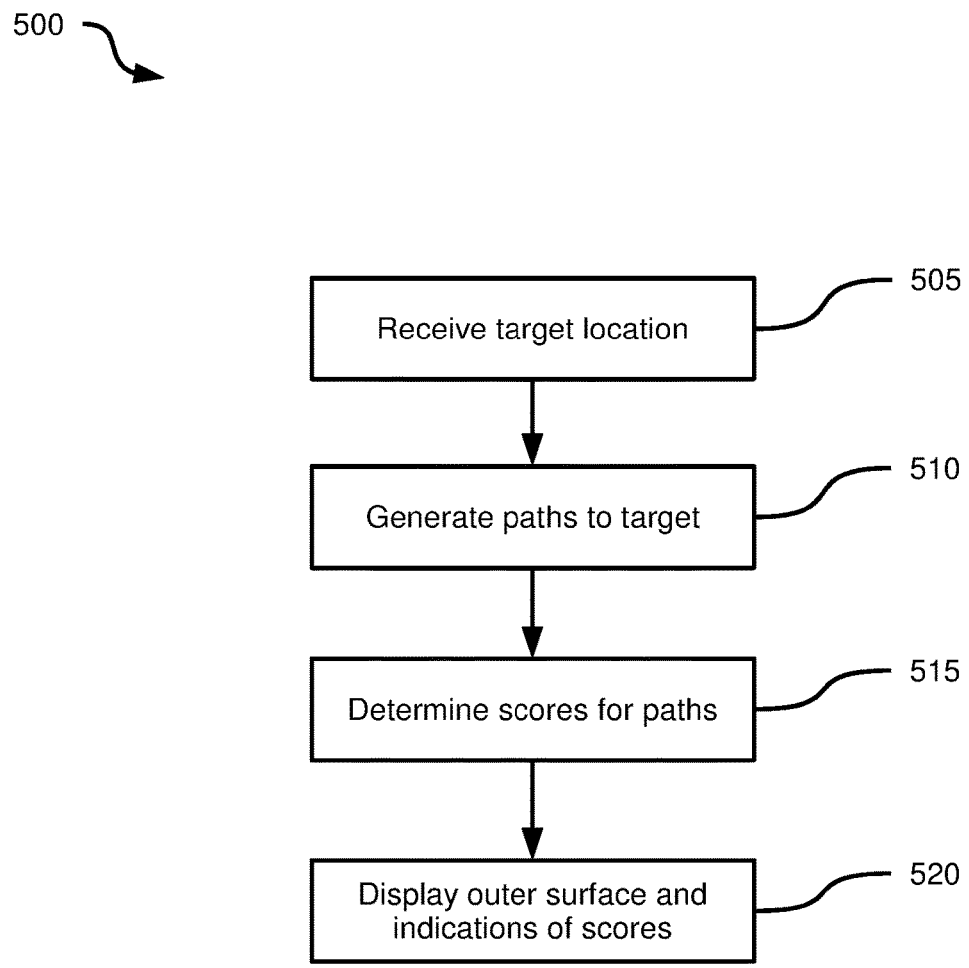
FIG. 5 depicts a method of evaluating and displaying engagement paths, according to a non-limiting embodiment.

Turning now to FIG. 5, a method 500 of evaluating and displaying engagement paths will be discussed in conjunction with its performance on computing device 200. Computing device 200, via the execution of application 216 (and the accompanying processing of data in repository 218), is configured to perform the blocks of method 500. Method 500 may, however, also be performed in other systems and by other computing devices.

Figure 6:
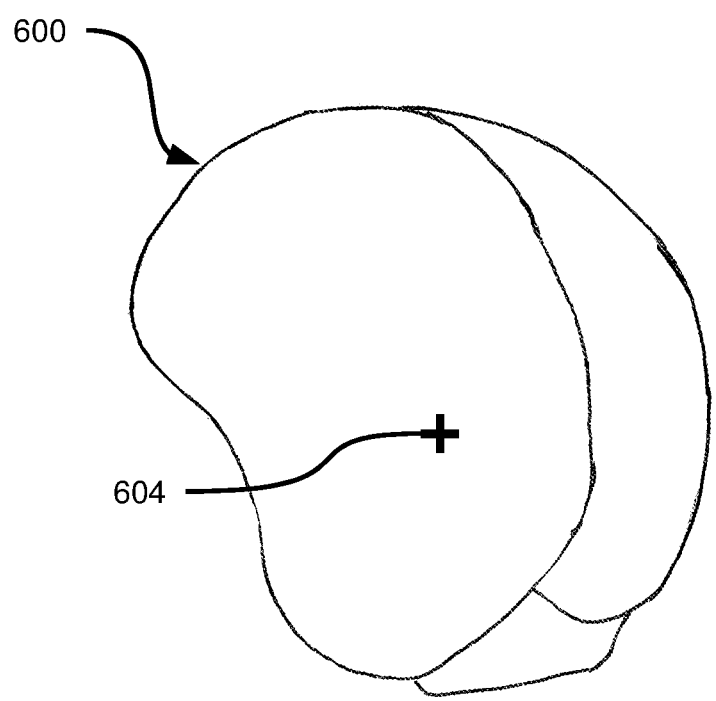
FIG. 6 depicts a simplified version of the image of FIG. 3, including a target location received by the computing device of FIG. 2, according to a non-limiting embodiment.

Beginning at block 505, computing device 200 is configured to receive an identifier of a target location within the volume depicted by image 300. In the present example, the identifier is a set of coordinates identifying a point within the volume. The mechanism by which computing device 200 receives the target location identifier is not particularly limited. For example, processor 202 can control display 110 to present image 300, and mouse/keyboard 210 can receive input in the form of a selection of a particular point on display 110, and transmit input data representative of that point to processor 202. In other embodiments, processor 202 can automatically select a target location based on other data within repository 218, such as the location of a tumor within the brain of patient 104. FIG. 6 depicts a simplified version 600 of image 300 in which the received target location 604 is also depicted. It is assumed that location 604 is within the volume depicted by image 600, as opposed to on the outer surface of the volume.

Returning to FIG. 5, having received a target location at block 505 computing device 200 is configured to automatically generate a plurality of paths from the outer surface of the volume depicted in image 600 to target location 604. Each path generated at block 510 is a straight line defined by a start point on the outer surface, and an end point at the target location. The number of paths generated at block 510 is not particularly limited, and can be selected based on the computational capacity of computing device 200, the resolution of image 600, and the like. In some embodiments, for example, a path can be generated at block 510 for every voxel defining the outer surface of the volume in image 600. In other words, every voxel of the outer surface in image 600 can be selected as a start point for a path. In other embodiments, paths may be generated with start points at regular spacing (e.g. in a grid, with each start point separated by ten voxels).

Figure 7:
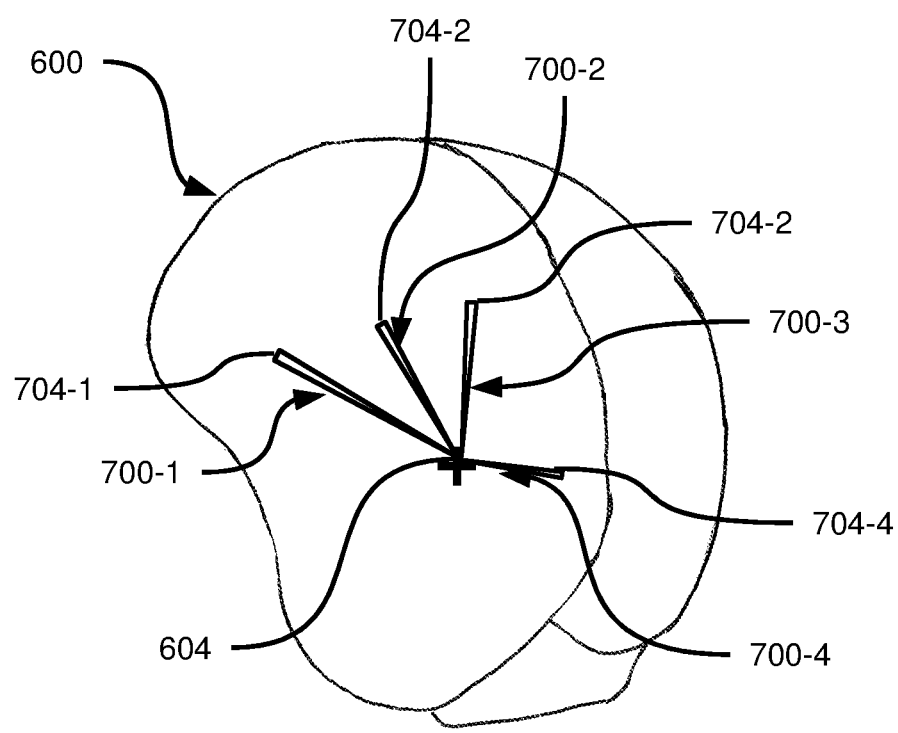
FIG. 7 depicts engagement paths generated by the computing device of FIG. 2 during the performance of the method of FIG. 5, according to a non-limiting embodiment.

FIG. 7 depicts four paths 700-1, 700-2, 700-3 and 700-4 (collectively referred to as paths 700, and generically referred to as a path 700; this nomenclature is used elsewhere herein) automatically generated by processor 202 at block 510. Paths 700 have respective start points 704-1, 704-2, 704-3 and 704-4, and all have the same end point (target 604).

The paths generated at block 510 are stored in memory 204, for example in repository 218. For example, the paths can be stored in a table containing a record for each path, with each record containing the start point location and the end point location within the volume depicted by image 600. In other examples, the paths can be stored as metadata in image 600 itself.

Returning to FIG. 5, responsive to generating the paths at block 510, at block 515 computing device 200 is configured to determine a score for each of the paths. In general, the score for each path is based on a comparison between the path and the anatomical data mentioned earlier. The scores determined at block 515 indicate the suitability of the paths for engagement with access port 106 (or other instruments). The suitability of a path of engagement for access port 106 is inversely proportional to a degree to which the path interferes with the anatomical structures defined by the anatomical data (e.g. by traversing the anatomical structures). As a result, a variety of actions can be performed by processor 202 at block 515, depending on the available anatomical data. Examples of those actions are depicted in FIG. 8.

Figure 8:
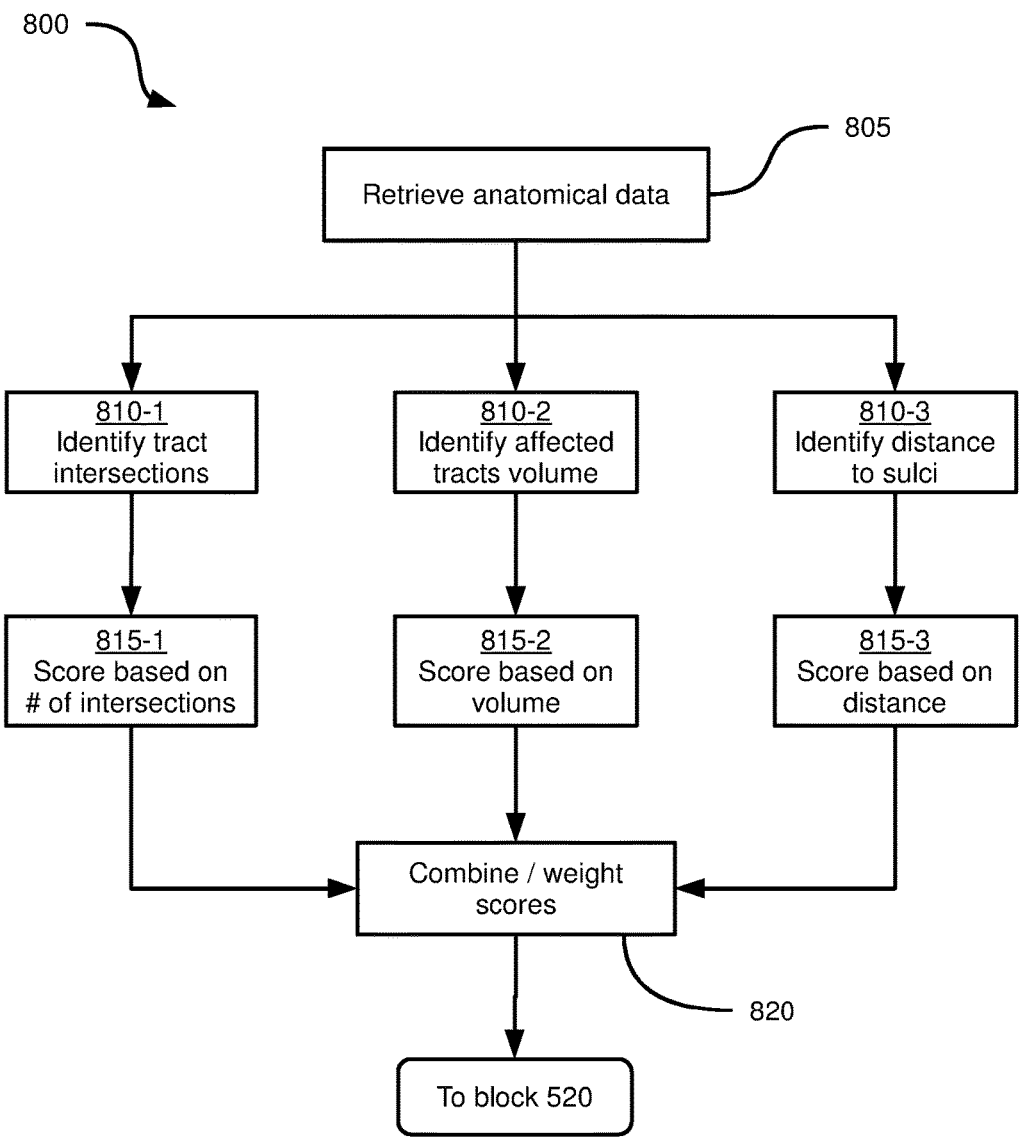
FIG. 8 depicts a method of scoring the engagement paths of FIG. 7, according to a non-limiting embodiment.

FIG. 8 depicts a method 800 of determining scores for the paths generated at block 510. In other words, method 800 is a method of performing block 515 of method 500. Method 800 is performed by computing device 200 for each path generated at block 510.

Beginning at block 805, processor 202 is configured to retrieve the anatomical data from memory 204. For example, processor 202 can retrieve tracts 404 at block 805. From block 805, processor 202 proceeds to at least one of blocks 810-1, 810-2 and 810-3. Which ones of blocks 810 are performed in any given instance of method 800 depends on what anatomical data is available. Blocks 810-1 and 810-2 can be performed if the anatomical data includes data defining diffusion tracts, such as tracts 404. Block 810-3 can be performed if the anatomical data includes data defining sulcal folds. It is contemplated, however, that even if the corresponding anatomical data is stored in memory 204, one or more of blocks 810 can be omitted. Blocks 810 can be performed in parallel, or sequentially.

At block 810-1, computing device 200 is configured to identify intersections between the path and tracts 404, and at block 815-1 computing device 200 is configured to assign a score to the path based on the number of intersections identified at block 810-1. Computing device 200 can also be configured to assign a score to the path based on the angles of the intersections between the path and tracts 404, as well as based on labels associated with tracts 404 in the anatomical data (for example, certain tracts labelled as corticospinal tracts may have a greater effect on score than others). The identification of intersections can be undertaken using conventional geometrical techniques, as the start and end points of the path are known, and the coordinates of tracts 404 are also known.

The score assigned at block 815-1 can take a variety of forms. For example, the score can be the number of intersections identified at block 810-1. In other examples, the score can be the number of intersections, normalized to a predefined range (e.g. zero to ten).

At block 810-2, computing device 200 is configured to identify a volume of tracts 404 affected by the path. In other words, rather than counting intersections between tracts 404 and the path, the volumes of all tracts among tracts 404 that are intersected by the path are summed at block 810-2. Tracts 404 generally represent nerve cells, or bundles of nerve cells, and a path that intersects a tract may therefore negatively affect the entire nerve cell or bundle represented by that tract. At block 815-2, computing device 200 assigns a score to the path based on the volume identified at block 810-2.

The score assigned at block 815-2 can take a variety of forms. For example, the score can be the volume of affected tracts identified at block 810-2 (e.g. the volume in cubic centimeters, or expressed as a number of voxels in image 600). In other examples, the score can be the volume of intersected tracts, normalized to a predefined range (e.g. zero to ten).

At block 810-3, computing device is configured to identify a distance between the path and the closest sulcus of the brain (sulci are not shown in the simplified image of FIG. 6, but are shown in FIG. 3). The identification of the closest sulcus, and of the distance between the path and the closest sulcus, can be performed using conventional geometrical methods. At block 815-3, computing device 200 is configured to assign a score to the path based on the distance from the path to the nearest sulcus.

The score assigned at block 815-3 can take a variety of forms. For example, the score can be the distance determined at block 810-3 (e.g. in millimeters). In other examples, the score can be the distance from block 810-3, normalized to a predefined range (e.g. zero to ten).

At block 820, computing device 200 is configured to combine the scores from blocks 815-1, 815-2 and 815-3 into a single score for the path. The combination can involve weighting in some examples. For instance, memory 204 can contain weighting factors indicating the relative importance of the scores assigned at blocks 815 in determining the combined score at block 820. In other examples, weighting can be omitted, and the combined score can be a simple average or sum of the scores from blocks 815. In the examples given above, the scores from blocks 815 are all inversely proportional with suitability of the path for insertion of access port 106. That is, a larger number of path intersections, a greater affected volume, and a larger distance to the nearest sulcus are all indicators that the path is less suitable than a path for which any of the above metrics are smaller. In some embodiments, the proportionality between score and suitability for the score from block 815-1, for example, may be different from the proportionality for the score from block 815-2. In such embodiments, at block 820 computing device 200 can be configured to modify the scores from blocks 815 to generate modified scores having the same proportionality as each other before combining the modified scores (e.g. by calculating the inverse of a score).

It is contemplated that when other anatomical features are defined in memory 204, additional branches (not shown) of method 800 can be performed. For example, when repository 218 contains anatomical data defining regions of the imaged volume of tissue indicated as being regions to avoid, a score can be assigned to each path based on whether or not the path intersects such regions. Such regions can be defined in a variety of ways, include via the receipt of input data from keyboard/mouse 210 at processor 202. Having generated a combined score for each path through repeated performances of blocks 805-820, processor 202 returns to block 520 of method 500.

At block 520, computing device 200 is configured to control display 110 to present at least the outer surface of image 600 and, at the locations on the outer surface of the start points generated at block 510, indications of the (combined, if applicable) scores of the paths corresponding to the start points.

Figure 9:
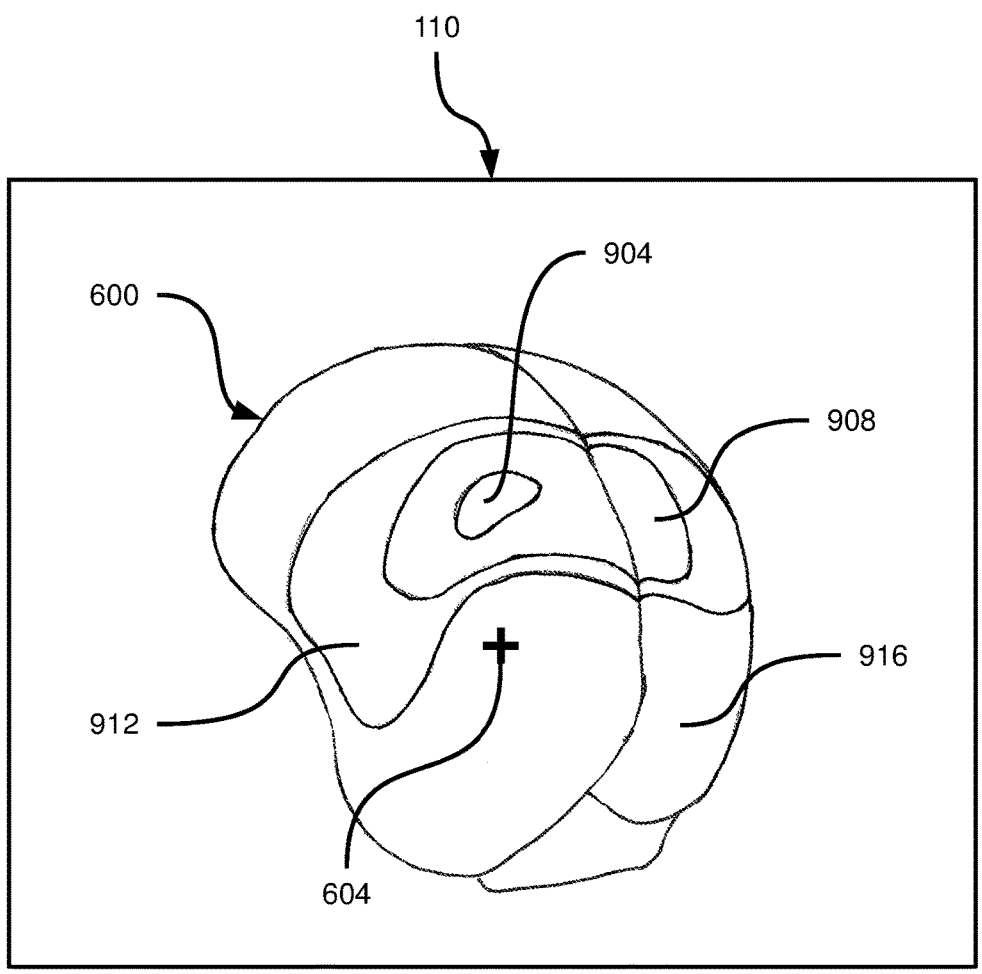
FIG. 9 depicts an interface rendered by the computing device of FIG. 2 including indications of the scores determined through the method of FIG. 5, according to a non-limiting embodiment.

The indications of the scores for each start point can be presented on display 110 in a variety of forms. Referring to FIG. 9, an example interface presented on display 110 at block 520 is depicted. Display 110, under the control of processor 202, presents image 600 and target location 604 (although target location 604 can be omitted in some embodiments), with an overlay having a plurality of regions. In particular, regions 904, 908, 912 and 916 are shown. The locations and sizes of regions 904, 908, 912 and 916 are generated by processor 202 based on a comparison between the scores from block 520 and a set of thresholds stored in memory 204. For example, region 904 is shaped and sized to contain all the start points of the paths with scores below a first threshold; region 908 is shaped and sized contain all the start points of the paths with scores above the first threshold but below a second threshold; region 908 is shaped and sized to contain all the start points of the paths with scores above the second threshold but below a third threshold; and region 912 is shaped and sized to contain all the start points of the paths with scores exceeding the third threshold.

In the examples above, the scores are contemplated as being inversely proportional to the suitability of the start points for entry of access port 106. In other words, the scores reflect the level of interference of the paths with anatomical structures. In other embodiments, where scores are directly proportional with suitability of the corresponding paths, the regions can be defined to contain start points that exceed the various thresholds, rather than fall below the thresholds. Thus, with directly proportional scores, region 904 can contain all the start points whose paths have scores greater than a first threshold, and region 908 can contain all the start points whose paths have scores greater than a second threshold, but below the first threshold. It is also contemplated that there can be more than one region for a given threshold. For example, there may be more than one cluster of start points having scores that satisfy the first threshold, separated by start points having scores that only satisfy the second threshold. In such cases, multiple regions 904 would be presented on display 110.

Regions 904, 908, 912 and 916 can be shaded or colour-coded to distinguish them from each other. Alternatively, or in addition to such shading or colour-coding, lines marking the borders between regions can be presented on display 110, as in FIG. 9. There can also be a greater or smaller number of regions, and a corresponding number of thresholds.

Figure 10:
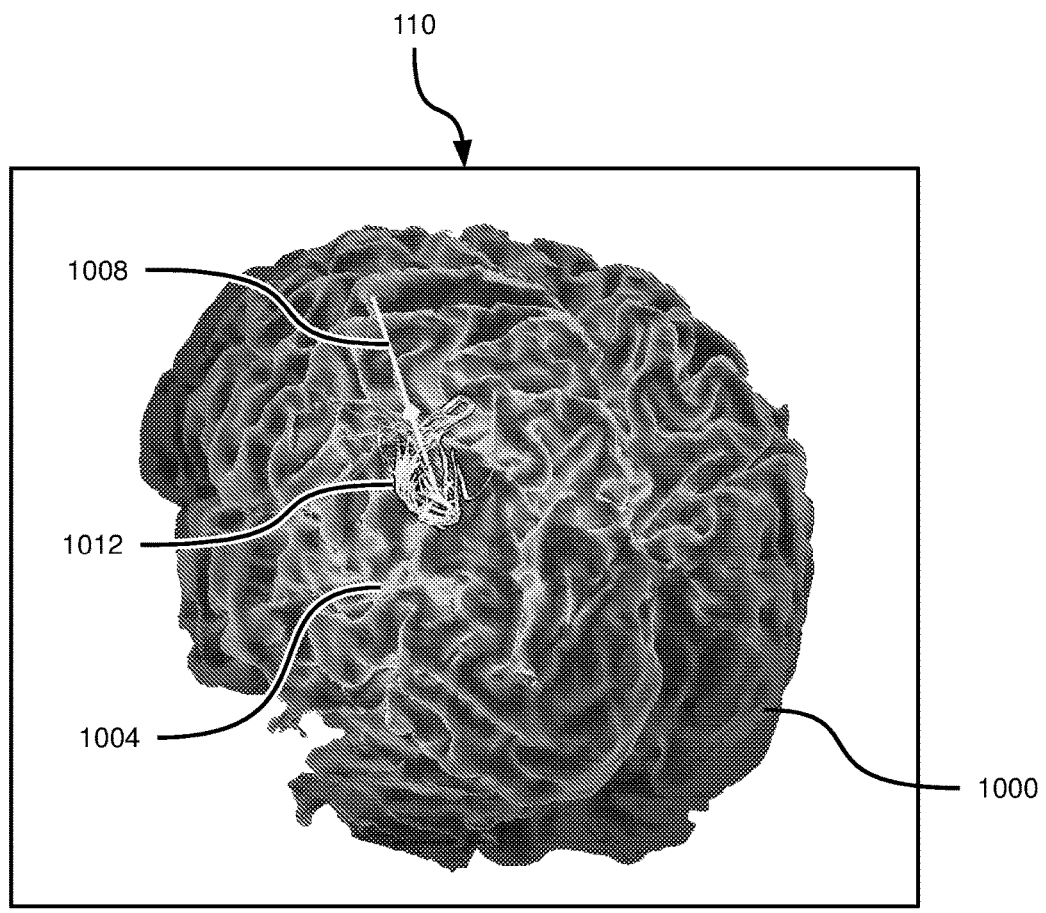
FIG. 10 depicts an interface rendered by the computing device of FIG. 2 including indications of the scores determined through the method of FIG. 5, according to another non-limiting embodiment.

In other embodiments, the above-mentioned thresholds can be omitted, and scores for each path can be converted directly into a brightness value, colour or the like. For example, each score may be scaled to a brightness value on a scale of zero (black) to two-hundred and fifty-five (white). The scaled scores can then be presented on display 110. An example of this implementation is shown in FIG. 10, in which the start points for paths having scores indicating low suitability have lower brightness values (for example, start point 1000) than the paths having scores indicating high suitability (for example, start point 1004). In other examples, rather than a brightness conversion leading to grey-scale values, scores can be scaled to the hexadecimal colour scale, having values from zero (000000 or black) to Ser. No. 16/777,215 (FFFFFF or white) and traversing a broad spectrum of colours in between. In still other examples, specific mappings of scores to colours can be stored in memory 204.

As seen in FIG. 10, even when regions are not employed as in FIG. 9, the entirety of the outer surface can nevertheless be shaded or colorized, if a path is generated for each voxel defining the outer surface. When a smaller number of paths are generated than there are voxels defining the outer surface, computing device 200 can still be configured to colorize or shade the entire outer surface by applying the above-mentioned colorization or shading to an area of the outer surface surrounding the start point (for example, a radius of ten voxels around the start point).

Also depicted on display 110 in the interface shown in FIG. 10 is a path marker 1008 and a subset 1012 of tracts 404. Processor 202 can be configured to automatically display path marker 1008 for the path having the greatest suitability for insertion of access port 106. In other embodiments, processor 202 can display path marker 1008 for any path selected, for example, via keyboard/mouse 210. Tract subset 1012 includes those tracts intersected by path marker 1008. Tract subset 1012 can be enabled and disabled, for example in response to input data received at processor 202 from keyboard/mouse 210.

Figure 11:
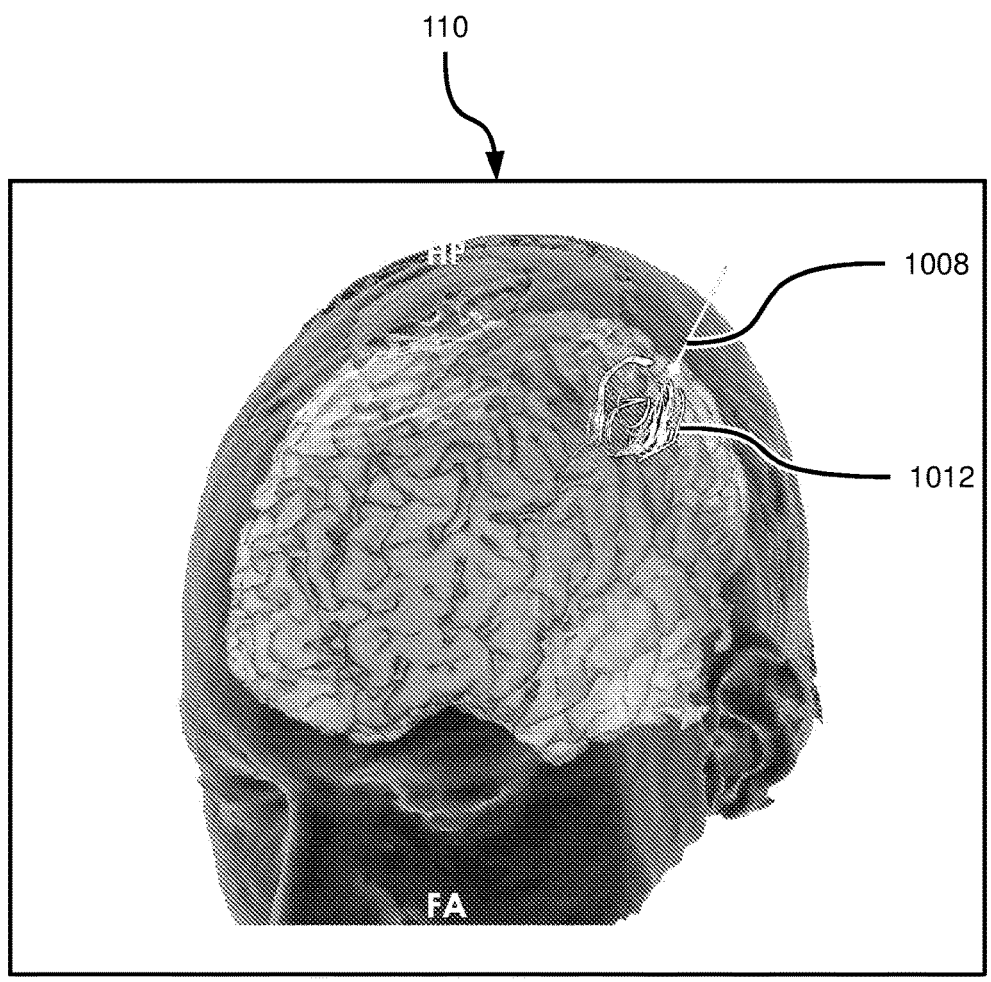
FIG. 11 depicts rendered by the computing device of FIG. 2 including indications of the scores determined through the method of FIG. 5, according to a further non-limiting embodiment.

Referring to FIG. 11, in some embodiments additional structures defined in the image in repository 218, the anatomical data, or both, can be presented on display 110. For example, in addition to the outer surface, marker 1008, and tract subset 1012 mentioned above, FIG. 11 depicts anatomical structures surrounding the brain of patient 104, particularly the skull and face of patient 104. When presented on display 110, such surrounding structures can be rendered translucently so as not to obscure the outer surface of the brain. In further embodiments, the outer surface itself can be rendered translucently so as to permit anatomical structures within the brain to be viewed.

In some additional variations, the performance of method 500 can be repeated during a single medical procedure to produce updated scores. For example, computing device 200 can receive additional anatomical data following a first performance of method 500. For example, the additional anatomical data can include one or more additional images, such as an ultrasound or OCT image obtained intraoperatively. Such intraoperative images may show tissue deformation caused by, for example, the removal of a portion of the skull of patient 104 to permit entry of access port 106 or other instrumentation.

The intraoperative images may reveal, therefore, that the initial target location has moved (alternatively, additional input data may be received at computing device 200 identifying an updated target location). Tracts 404 may also have shifted in response to tissue deformation. Therefore, following the receipt of intraoperative anatomical data, computing device 200 can be configured to receive or compute an updated target location (block 505), and to generate an updated set of paths to the target location (block 510). Responsive to the generation of updated paths, computing device 200 can score and display the updated paths (blocks 515 and 520) as discussed above. In implementations where the intraoperative image data is received from an imaging probe being inserted into patient 104's brain, updated scoring can therefore be generated by computing device 200 in near real-time. In alternate embodiments, determining the score may include determining a plurality of scores respective to different types of anatomical features and/or combining the scores.

Persons skilled in the art will appreciate that there are yet more alternative implementations and modifications possible for implementing the embodiments, and that the above implementations and examples are only illustrations of one or more embodiments. The scope, therefore, is only to be limited by the claims appended hereto.

We claim:

1. A method of displaying surgical path data in a computing device having an input device, a display, a memory and a processor interconnected with the input device, the display, and the memory, the method comprising:
storing, in the memory, (i) an image of a volume of patient tissue having an outer surface, and (ii) anatomical data defining a plurality of anatomical features of the volume, the anatomical features including a plurality of sulci and a plurality of additional anatomical features;
receiving, at the processor, an identifier of a target location within the volume;
at the processor, generating a plurality of paths from the outer surface to the target location, each path having a start point located on the outer surface, and an end point at the target location;
for each of the plurality of paths, determining a score at the processor by:
identifying a nearest one of the sulci to the respective path, and determining a first score for the respective path that is inversely proportional to a distance between the respective path and the nearest sulcus;
determining a second score that is inversely proportional to a number of the additional anatomical features intersected by the path; and
combining the first score and the second score; and
controlling the display to present the outer surface and, at the locations of the start points, indications of the respective scores of the paths corresponding to the start points.

2. The method of claim 1, wherein the additional anatomical features include a plurality of blood vessels, and wherein determining the second score comprises identifying, at the processor, a volume of the blood vessels intersected by the path.

3. The method of claim 1, wherein determining the score comprises determining a third score respective to further anatomical features, and combining the third score with the first and second scores.

4. The method of claim 1, wherein controlling the display comprises converting the scores to display values, and presenting the display values as the indications of the scores.

5. The method of claim 4, wherein the display values comprise at least one of a brightness and a colour.

6. A computing device for displaying surgical path data, comprising:
an input device;
a display;
a memory storing (i) an image of a volume of patient tissue having an outer surface, and (ii) anatomical data defining anatomical features of the volume, the anatomical features including a plurality of sulci and a plurality of additional anatomical features; and
a processor interconnected with the input device, the display, and the memory, the processor configured to:
receive an identifier of a target location within the volume;
generate a plurality of paths from the outer surface to the target location, each path having a start point located on the outer surface, and an end point at the target location;
for each of the plurality of paths, determine a score by:
identifying a nearest one of the sulci to the respective path, and determining a first score for the respective path that is inversely proportional to a distance between the respective path and the nearest sulcus;

determining a second score that is inversely proportional to a number of the additional anatomical features intersected by the path; and combining the first score and the second score; and control the display to present the outer surface and, at the locations of the start points, indications of the respective scores of the paths corresponding to the start points.

7. The computing device of claim 6, wherein the additional anatomical features include a plurality of blood vessels, and wherein the processor is configured to determine the second score by identifying a volume of the blood vessels intersected by the path.

8. The computing device of claim 6, wherein the processor is configured to determine the score by determining a third score respective to further anatomical features, and combining the third score with the first and second scores.

9. The computing device of claim 6, wherein controlling the display comprises converting the scores to display values, and presenting the display values as the indications of the scores.

10. The computing device of claim 9, wherein the display values comprise at least one of a brightness and a colour.

11. A non-transitory computer-readable medium storing a plurality of computer-readable instructions for execution by a processor of a computing device having an input device, a display, and a memory connected to the processor, to perform a method comprising:

storing, in the memory, (i) an image of a volume of patient tissue having an outer surface, and (ii) anatomical data defining anatomical features of the volume, the anatomical features including a plurality of sulci and a plurality of additional anatomical features;

receiving, at the processor, an identifier of a target location within the volume;

at the processor, generating a plurality of paths from the outer surface to the target location, each path having a start point located on the outer surface, and an end point at the target location;

for each of the plurality of paths, determining a score at the processor by:

identifying a nearest one of the sulci to the respective path, and determining a first score for the respective path that is inversely proportional to a distance between the respective path and the nearest sulcus;

determining a second score that is inversely proportional to a number of the additional anatomical features intersected by the path; and combining the first score and the second score; and controlling the display to present the outer surface and, at the locations of the start points, indications of the respective scores of the paths corresponding to the start points.

12. The non-transitory computer-readable medium of claim 11, wherein the additional anatomical features include a plurality of blood vessels, and wherein determining the second score comprises identifying, at the processor, a volume of the blood vessels intersected by the path.

13. The non-transitory computer-readable medium of claim 11, wherein determining the score comprises determining a third score respective to further anatomical features, and combining the third score with the first and second scores.

14. The non-transitory computer-readable medium of claim 11, wherein controlling the display comprises converting the scores to display values, and presenting the display values as the indications of the scores.

15. The non-transitory computer-readable medium of claim 11, wherein the display values comprise at least one of a brightness and a colour.

* * * * *